United States Patent [19]
Denis et al.

[11] Patent Number: 5,625,096
[45] Date of Patent: Apr. 29, 1997

[54] HYDROXYCARBONYLATION OF BUTADIENE

[75] Inventors: Phillipe Denis, Decines; Carl Patois, Lyons; Robert Perron, Charly, all of France

[73] Assignee: Rhone-Poulenc Chimie, Courbevoie Cedex, France

[21] Appl. No.: 325,077

[22] Filed: Oct. 19, 1994

[30] Foreign Application Priority Data

Oct. 19, 1993 [FR] France .................... 93 12666

[51] Int. Cl.$^6$ .................................. C07C 51/14
[52] U.S. Cl. ............................. 562/522; 562/598
[58] Field of Search ........................ 562/522, 598

[56] References Cited

U.S. PATENT DOCUMENTS

| | | | |
|---|---|---|---|
| 5,041,642 | 8/1991 | Jenck | 562/522 |
| 5,288,903 | 2/1994 | Bunel et al. | 562/598 |

FOREIGN PATENT DOCUMENTS

| | | |
|---|---|---|
| 4735364 | 1/1966 | Australia . |
| 1402383 | 6/1994 | France . |

Primary Examiner—Samuel Barts
Assistant Examiner—Rosalynd A. Williams
Attorney, Agent, or Firm—Burns, Doane, Swecker & Mathis, L.L.P.

[57] ABSTRACT

Butadiene or derivative thereof is selectively hydroxycarbonylated into at least one pentenoic acid (the pentenoic acids are themselves facilely converted, via hydroxycarbonylation, into adipic acid, a basic starting material for the production of nylon 66 polymers), by reacting same with carbon monoxide and water, at a pressure greater than atmospheric, in the presence of a catalytically effective amount of (1) a palladium catalyst which is soluble in the medium of reaction and (2) crotyl chloride, the amount of the crotyl chloride being at least two mol thereof per mole of palladium values and said palladium values/ crotyl chloride at least in part comprising a palladium/crotyl pi-complex, and the amount of water present in the medium of reaction being no greater than about 20% by weight thereof.

22 Claims, No Drawings

HYDROXYCARBONYLATION OF BUTADIENE

BACKGROUND OF THE INVENTION

1. Field of the Invention

The present invention relates to the hydroxycarbonylation of butadiene and/or derivatives thereof, into pentenoic acids, and more especially, to the hydroxycarbonylation of butadiene via catalyzed reaction with carbon monoxide and water.

2. Description of the Prior Art

One known process for the preparation of adipic acid, one of the two basic constituents of nylon or polyamide 66 polymers, comprises the double carbonylation of butadiene or derivatives thereof.

Although it may be envisaged to carry out the two hydroxycarbonylations to convert butadiene into adipic acid in a single step, in actual practice it transpires that the two reactions must be carried out successively, if it is desired to obtain sufficiently high selectivities as to provide an economically viable industrial process.

U.S. Pat. No. 3,509,209 describes the hydroxycarbonylation of various olefins, including butadiene, via reaction with carbon monoxide and water, in the presence of hydrochloric or hydrobromic acid and a palladium-containing catalyst, at a temperature of 15° C. to 300° C. and at a pressure of 1 to 1,000 bar, preferably from 10 to 200 bar.

Under the reaction conditions described, it is observed that the yields of pentenoic acids are very low and that, indeed, very often the compound obtained is valerolactone.

FR-A-2,529,885 describes a process for the preparation of beta,gamma-unsaturated acids such as pentenoic acids, by carbonylation of a conjugated diene (more particularly butadiene) in the presence of water, a halogenhydracid, a palladium-based catalyst and a quaternary onium salt of an element selected from among nitrogen, phosphorus and arsenic.

This process gives good results, but it requires the use of a relatively large amount of a quaternary onium salt, which compound is expensive and the presence of which tends to complicate the final treatment of the mixtures at the end of the reaction.

SUMMARY OF THE INVENTION

Accordingly, a major object of the present invention is the provision of an improved process for the hydroxycarbonylation of butadiene and derivatives thereof that is highly selective in respect of value-added final products, notably in respect of the pentenoic acids, but which does not require the presence of a quaternary onium salt.

Briefly, the present invention features a process for the hydroxycarbonylation of butadiene and derivatives thereof via reaction with carbon monoxide and water, at a pressure greater than atmospheric pressure and in the presence of a palladium catalyst which is soluble in the reaction medium, as well as in the presence of a co-catalytically effective amount of crotyl chloride, in an amount of crotyl chloride of at least two mol per mole of palladium, said palladium being at least partly in the form of a crotyl pi-complex, and the water being present in the reaction medium in an amount less than or equal to 20% by weight relative to the weight of the reaction mixture.

DETAILED DESCRIPTION OF BEST MODE AND PREFERRED EMBODIMENTS OF THE INVENTION

More particularly according to the present invention, by "butadiene derivatives" is especially intended allylic butenols, for example 3-buten-2-ol, 2-buten-1-ol and mixtures thereof and addition compounds of hydrogen chloride with butadiene (chlorobutenes), principally crotyl chloride. In the process of the invention, butadiene, one or more of the derivatives thereof, or mixtures of butadiene with one or more of its derivatives, may be used. Butadiene, or mixtures containing major amounts of butadiene, nevertheless are the preferred starting materials.

The crotyl/palladium pi-complex catalyst may be introduced into the reaction medium, or may be formed therein in situ from Pd halides, more particularly the chloride, from Pd carboxylates, in particular the acetate, or, alternatively, from finely divided palladium metal.

The amount of the pi-crotyl/palladium catalyst employed in the process of the invention may vary over a wide range. From $10^{-5}$ mol to 0.2 mol of Pd per mole of butadiene or of butadiene derivative employed in the reaction, preferably from $10^{-4}$ mol to 0.1 mol per mole, is typically used.

Other than the pi-crotyl/palladium catalyst, palladium in another, less active form (for example Pd metal or Pd chloride) may also be present in the reaction medium in a variable amount. However, in an industrial process, it is preferable that all or essentially all of the palladium be in an active form which is soluble in the medium of reaction, for example pi-crotyl/palladium, optionally with palladium chloride.

The crotyl/palladium pi-complex may be prepared, for example, by reacting a palladium salt, e.g., palladium chloride, with crotyl chloride in a solvent which may be a water/methanol admixture. The mixture is stirred, generally at room temperature, advantageously under a gentle stream of carbon monoxide. The pi-crotyl/palladium complex precipitates and, after an optional degassing step, the mixture is poured into water and then extracted using a suitable organic solvent, such as chloroform. The complex is subsequently isolated from the organic solution by evaporation of the solvent.

The crotyl chloride promotor may be introduced into the reaction mixture, or may be formed therein in situ, from butadiene and/or from 2-buten-1-ol and hydrochloric acid.

It is preferably present, in moles per mole, in amounts of from 5 to 10 times the amount of palladium, although it may be present in greater proportions, since it may comprise all or some of the substrate to be hydroxycarbonylated.

Overall, it is preferable to have a Cl/Pd molar ratio in the reaction medium of less than or equal to 100 and preferably of less than or equal to 20, because such high ratios have an adverse effect on the reaction kinetics.

As indicated above, the water concentration of the reaction mixture should be maintained at a value equal to or less than 20% by weight relative to the weight of said mixture. This is because the water concentration has an unfavorable effect on the reaction kinetics. This water concentration will preferably be maintained at a value equal to or less than 8% weight by weight and even more preferably at a value equal to or less than 5%.

As water is a reactant which is essential for the hydroxycarbonylation reaction, one preferred embodiment of the process of this invention comprises injecting this water progressively as the reaction proceeds, thus permitting its concentration in the reaction mixture to be maintained at a very low value, while at the same time allowing the reaction to occur.

Although the presence of a third solvent is not excluded, the reaction is generally carried out without any solvent other than the reactants themselves, or the reaction products. It may also be advantageous to introduce a pentenoic acid and more particularly, 3-pentenoic acid, from the beginning of the hydroxycarbonylation reaction, in order to minimize side reactions.

On an industrial scale, recycling of the catalyst, the promoter and the unreacted butadiene may result in the introduction of greater or lesser amounts of other compounds into the reaction medium, in particular of byproducts formed during the hydroxycarbonylation reaction. Thus, the reaction mixtures may, for example, contain butenes, gamma-valerolactone, valeric acid, adipic acid, 2-methylglutaric acid, 2-ethylsuccinic acid, 2-methylbutanoic acid and 2-methylbutenoic acids. Taking account of the fact that the subject process may be carried out continuously, the amounts of these compounds present may attain a value of up to 90% by weight of the reaction mixture employed in the hydroxycarbonylation reaction.

The butadiene concentration is an important parameter of the reaction, in particular as regards the stability of the palladium catalyst, namely, essentially maintaining same in solution in the reaction mixture. It has thus been observed that it is not desirable to have less than 0.2% by weight of butadiene present relative to the total weight of the reaction mixture. When the process is carried out discontinuously, conversion of the butadiene or derivatives thereof will preferably be limited such that the reaction mixture contains at least 0.5% by weight of said butadiene or derivatives thereof.

The butadiene concentration is also preferably maintained at a value equal to or less than 50% of the reaction mixture on a weight for weight basis, and even more particularly at a value less than or equal to 30%, when the process is carried out discontinuously, and at a value less than or equal to 10% when the process is performed continuously.

Whereas the palladium catalyst tends to precipitate in a large proportion in the form of insoluble palladium metal when the hydroxycarbonylation of butadiene is carried out under conditions different from those of the process of this invention, it is observed, on the contrary, that under the above conditions the catalyst retains a marked stability.

On an industrial scale, it is a very advantageous to introduce only liquid phases into the apparatus and thus, as far as is possible, to avoid the presence of solids in suspension. It is this, in particular, which the present process enables.

The hydroxycarbonylation reaction may be carried out at a temperature which generally ranges from 60° C. to 230° C. and preferably from 90° C. to 200° C., and at a pressure at the reaction temperature of 50 to 500 bar and preferably of 100 to 300 bar.

The partial pressure of carbon monoxide, measured at 25° C., advantageously ranges from 25 bar to 440 bar and preferably from 55 bar to 240 bar.

As indicated above, the process of the present invention may be carried out continuously or discontinuously. Depending upon the particular embodiment selected, whether continuously or discontinuously, it will therefore be necessary to adapt the various operating conditions described above.

In order to further illustrate the present invention and the advantages thereof, the following specific examples are given, it being understood that same are intended only as illustrative and in nowise limitative.

EXAMPLE 1

(1) Preparation of the crotyl/Pd chloride pi-complex 5.04 g of $PdCl_2$, 3.37 g of NaCl, 50 $cm^3$ of methanol, 15 $cm^3$ of water, 8.03 g of crotyl chloride and an additional 20 $cm^3$ of methanol were successively charged into a 150 $cm^3$ glass round-bottomed flask.

The heterogeneous mixture was stirred and progressively became dark brown and cloudy. The solution was subsequently treated, while stirring, with a gentle stream of carbon monoxide (at bubble rate) for one hour. The mixture became clear and a yellow precipitate formed. The stirring and the stream of CO were terminated and the solution was permitted to stand for one hour and was then poured into 300 $cm^3$ of water and extracted 5 times with 50 $cm^3$ of chloroform. The resulting straw-yellow organic phase was washed 2 times with 100 $cm^3$ of water, dried over disodium sulfate overnight and the solvent was then evaporated off. 3.35 g of a pale yellow solid were thus recovered, which product had a purity of greater than 94% (assay by Nuclear Magnetic Resonance: NMR).

(2) Hydroxycarbonylation of butadiene

The following reactants were successively charged into a 50 $cm^3$ glass flask:

| | |
|---|---|
| (i) pi-crotyl-Pd chloride: | 0.9 mmol |
| (ii) crotyl chloride: | 6.2 mmol |
| (iii) $H_2O$: | 100 mmol |
| (iv) 3-pentenoic acid: | 20 g (200 mmol) |
| (v) butadiene: | 100 mmol. |

The butadiene was introduced last, by condensation (cold wall at −78° C.) from a gate.

The flask was placed in a 125 $cm^3$ autoclave; the autoclave was placed in an oven incorporating agitation by shaking, connected to a system for the supply of gas at high pressure, and a pressure of 100 bar of CO was established at room temperature.

The temperature was subsequently adjusted to 140° C. with agitation over a period of 25 min. At this temperature, the pressure in the autoclave was adjusted to 200 bar by the introduction of CO and it was maintained constant at this value by means of a CO tank under pressure for 30 min.

The agitation was then stopped, the autoclave was cooled and degassed and the gases and the solution obtained were analyzed by gas chromatography (GC).

The following results were obtained:

| | |
|---|---|
| (a) Degree of conversion of butadiene (ECBD): | 92% |
| (b) Yield (Yd) of 3-pentenoic acid (P3) relative to the butadiene converted: | 89.5% |
| (c) Yd of adipic acid (A1): | 0.1% |
| (d) Yd of 2-methylglutaric acid (A2): | 4.1% |
| (e) Yd of 2-ethylsuccinic acid (A3): | 1.8% |
| (f) Yd of gamma-valerolactone (VAL): | 0.7% |
| (g) Yd of 2-pentenoic acid (P2): | 0.3% |
| (h) Yd of butenes (C4): | 0.6% |
| (i) Yd of methylbutenoic acids and methylbutanoic acid (MB): | 2.4% |

At the end of the test, all of the palladium charged remained in solution.

The production efficiency of the test was 500 g P3/liter of reactor/hour.

EXAMPLE 2

Procedure (2) of Example 1 was repeated with the same charges, except for the amount of water, which was 50 mmol instead of 100 mmol.

The temperature and pressure conditions were the same as in Example 1.

The same yields were obtained for the various products formed, but the production efficiency of the test was 1200 g P3/liter of reactor/hour.

EXAMPLE 3

Procedure (2) of Example 1 was repeated with the following charges:

| | | |
|---|---|---|
| (i) Pd acetate: | 0.9 mmol | |
| (ii) crotyl chloride: | 7.2 mmol | |
| (iii) H$_2$O: | 100 mmol | |
| (iv) 3-pentenoic acid: | 20 g (200 mmol) | |
| (v) butadiene: | 100 mmol. | |

The apparatus and the experimental procedure were the same as in Example 1.

The operating conditions were: 140° C.; 200 bar at this temperature; 30 min at this temperature and pressure.

The following results were obtained:

| | |
|---|---|
| (a) EC of butadiene: | 87% |
| (b) Yd of 3-pentenoic acid (P3): | 91% |
| (c) Yd of adipic acid (A1) | 0.1% |
| (d) Yd of 2-methylglutaric acid (A2): | 3% |
| (e) Yd of 2-ethylsuccinic acid (A3): | 2% |
| (f) Yd of gamma-valerolactone (VAL): | 0.8% |
| (g) Yd of 2-pentenoic acid (P2): | 0.2% |
| (h) Yd of butenes (C4): | 0.3% |
| (i) Yd of methylbutenoic acids and methylbutanoic acid (MB): | 2% |

At the end of the test, 97% of the palladium charged remained in solution.

The production efficiency of the test was 500 g P3/liter of reactor/hour.

EXAMPLES 4 TO 8

Procedure (2) of Example 1 was repeated with the following charges:

| | |
|---|---|
| (i) pi-crotyl-Pd chloride (prepared in Example 1) | 0.9 mmol |
| (ii) crotyl chloride: | 6.2 mmol |
| (iii) H$_2$O: | 100 mmol |
| (iv) 3-pentenoic acid: | 20 g (200 mmol) |
| (v) butadiene: | 100 mmol. |

The apparatus and the experimental procedure were the same as in Example 1.

The operating conditions were: 140° C.; 200 bar at this temperature; 25 min at this temperature and pressure.

A duration of 25 min was selected such as to attain an EC of butadiene of approximately 80%. After a first hydroxycarbonylaton operation, the agitation was stopped, the autoclave was cooled and degassed and the homogeneous solution obtained was placed under reduced pressure, in order to distill off the 3-pentenoic acid formed (between 5 and 7 g).

The distillation residue was still homogeneous and it was recycled to the glass flask, with fresh charges of crotyl chloride (6.2 mmol), water (100 mmol) and butadiene (100 mmol).

5 successive tests of the hydroxycarbonylation of butadiene were thus carried out under the same operating conditions.

The distillates obtained and the final distillation residue were analyzed by GC.

The following results were obtained (over the series of 5 tests):

| | |
|---|---|
| (a) EC of butadiene: | 80% |
| (b) Yd of 3-pentenoic acid (P3): | 93% |
| (c) Yd of adipic acid (A1): | 0% |
| (d) Yd of 2-methylglutaric acid (A2): | 2.6% |
| (e) Yd of 2-ethylsuccinic acid (A3): | 0.9% |
| (f) Yd of gamma-valerolactone (VAL): | 0.8% |
| (g) Yd of 2-pentenoic acid (P2): | 0% |
| (h) Yd of methylbutenoic acids and methylbutanoic acid (MB): | 1.7% |

At the end of the test, all of the palladium charged remained in solution.

The production efficiency of the test was 415 g P3/liter of reactor/hour.

EXAMPLES 9 AND 10

Procedure (2) of Example 1 was repeated with the following charges:

| | |
|---|---|
| (i) pi-crotyl-Pd chloride: | 0.9 mmol |
| (ii) crotyl chloride: | 7.1 mmol |
| (iii) H$_2$O: | 120 mmol |
| (iv) 3-pentenoic acid: | 20 g (200 mmol) |
| (v) butadiene: | 100 mmol. |

The reactants were charged directly to the autoclave (made of nickel/molybdenum alloy of trademark Hastelloy B2) and the experimental procedure was the same as in Example 1.

The operating conditions were: 140° C.; 200 bar at this temperature; 20 min at this temperature and pressure.

The following results were obtained:

| | |
|---|---|
| (a) EC of butadiene: | 81% |
| (b) Yd of 3-pentenoic acid (P3): | 92% |
| (c) Yd of adipic acid (A1): | 0.1% |
| (d) Yd of 2-methylglutaric acid (A2): | 3.6% |
| (e) Yd of 2-ethylsuccinic acid (A3): | 2.2% |
| (f) Yd of gamma-valerolactone (VAL): | 1.8% |
| (g) Yd of 2-pentenoic acid (P2): | 0.1% |
| (h) Yd of butenes (C4): | 0.1% |
| (i) Yd of methylbutenoic acids and methylbutanoic acid (MB): | 2.4% |

At the end of the test, all of the palladium charged remained in solution.

The final butadiene concentration was 2% by weight of the reaction mixture.

The production efficiency was 800 g P3/liter of reactor/hour.

The procedure of Example 9 was repeated with the same charges and the same operating conditions, but it was maintained for 40 min at the reaction temperature and pressure instead of 20 min (Example 10).

The yields obtained were the same as in Example 9, but the final butadiene concentration was 0.35% by weight in the reaction mixture.

It was observed that 20% of the catalyst charged had precipitated in the form of Pd metal.

EXAMPLE 11

Procedure (2) of Example 1 was repeated with the following charges:

| | |
|---|---|
| (i) pi-crotyl-Pd chloride: | 0.9 mmol |
| (ii) crotyl chloride: | 112 mmol |
| (iii) H$_2$O: | 100 mmol |
| (iv) 3-pentenoic acid: | 20 g (200 mmol) |
| (v) butadiene: | 100 mmol. |

The apparatus and the experimental procedure were the same as in Example 1.

The operating conditions were: 140° C.; 200 bar at this temperature; 40 min at this temperature and pressure.

The following results were obtained:

| | |
|---|---|
| (a) EC of crotyl chloride: | 90% |
| (b) Yd of 3-pentenoic acid (P3): | 26% |
| (c) Yd of adipic acid (A1): | 0.1% |
| (d) Yd of 2-methylglutaric acid (A2): | 0.1% |
| (e) Yd of 2-ethylsuccinic acid (A3): | 6.0% |
| (f) Yd of gamma-valerolactone (VAL): | 17.0% |
| (g) Yd of 2-pentenoic acid (P2): | 0.2% |
| (h) Yd of methylbutenoic acids and methylbutanoic acid (MB): | 2.0% |

The production efficiency was 130 g P3/liter of reactor/hour.

COMPARATIVE EXAMPLE

Employing a High Water Concentration

Procedure (2) of Example 1 was repeated with the following charges:

| | |
|---|---|
| (i) pi-crotyl-Pd chloride: | 0.9 mmol |
| (ii) crotyl chloride: | 7.1 mmol |
| (iii) H$_2$O: | 500 mmol |
| (iv) 3-pentenoic acid: | 15 g (150 mmol) |
| (v) butadiene: | 100 mmol. |

The apparatus and the experimental procedure were the same as in Example 1.

The operating conditions were: 140° C.; 200 bar at this temperature; 103 min at this temperature and pressure.

The following results were obtained:

| | |
|---|---|
| (a) EC of butadiene: | 72% |
| (b) Yd of 3-pentenoic acid (P3): | 79% |
| (c) Yd of adipic acid (A1): | 0.4% |
| (d) Yd of 2-methylglutaric acid (A2): | 2% |
| (e) Yd of 2-ethylsuccinic acid (A3): | 0.3% |
| (f) Yd of gamma-valerolactone (VAL): | 13% |
| (g) Yd of butenes (C4): | 1% |
| (h) Yd of methylbutenoic acids and methylbutanoic acid (MB): | 5% |

The production efficiency was 87 g P3/liter of reactor/hour.

At the end of the test, although the butadiene concentration was still 2%, it was observed that approximately 25% of the catalyst charged had precipitated in the form of Pd metal.

Furthermore, the yield of 3-pentenoic acid was only 79% and the production efficiency 87 g P3/l/h.

EXAMPLE 12

Procedure (2) of Example 1 was repeated with the following charges:

| | |
|---|---|
| (i) pi-crotyl-Pd chloride: | 0.9 mmol |
| (ii) crotyl chloride: | 7.1 mmol |
| (iii) H$_2$O: | 100 mmol |
| (iv) 2-methylglutaric acid: | 15 g (103 mmol) |
| (v) 2-ethylsuccinic acid: | 5 g (34 mmol) |
| (vi) butadiene: | 100 mmol. |

The apparatus and the experimental procedure were the same as in Example 1.

The operating conditions were: 140° C.; 200 bar at this temperature; 70 min at this temperature and pressure.

The following results were obtained:

| | |
|---|---|
| (a) EC of butadiene: | 78% |
| (b) Yd of 3-pentenoic acid (P3): | 95% |
| (c) Yd of gamma-valerolactone (VAL): | 0.6% |
| (d) Yd of butenes (C4): | 0.8% |
| (e) Yd of methylbutenoic acids and methylbutanoic acid (MB): | 4% |

The diacids formed, representing very low amounts relative to the amounts employed at the beginning of the test, were not assayed.

At the end of the test, all of the palladium charged remained in solution.

The production efficiency was 164 g P3/liter of reactor/hour.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxycarbonylation of butadiene or derivative thereof into at least one pentenoic acid, comprising reacting said butadiene or derivative thereof with carbon monoxide and water, at a pressure greater than atmospheric, in the presence of a catalytically effective amount of (1) a palladium catalyst which is soluble in the medium of reaction and (2) crotyl chloride, the amount of said crotyl chloride being at least two mol thereof per mole of palladium values and said palladium values/crotyl chloride at least in part comprising a palladium/crotyl pi-complex, and the amount of water present in said medium of reaction being no greater than about 20% by weight thereof wherein butadiene is present in an amount of at least 0.2% by weight relative to the total weight of the reaction mixture and the medium of reaction has substantially no amount of a quaternary onium salt.

2. The process as defined by claim 1, carried out at a total pressure of from 50 bar to 500 bar.

3. The process as defined by claim 2, carried out at a total pressure of from 100 bar to 300 bar.

4. The process as defined by claim 1, carried out at a partial pressure of carbon monoxide, measured at 25° C., of from 25 bar to 440 bar.

5. The process as defined by claim 4, carried out at a partial pressure of carbon monoxide of from 55 bar to 240 bar.

6. The process as defined by claim 1, wherein the amount of palladium values in said medium of reaction comprises from $10^{-5}$ mol to 0.2 mol per mole of said butadiene or derivative thereof.

7. The process as defined by claim 1, said amount of palladium values comprising from $10^{-4}$ mol to 0.1 mol per mole of said butadiene or derivative thereof.

8. The process as defined by claim 1, wherein the amount of crotyl chloride in said medium of reaction comprises from 5 to 10 times the molar amount of palladium values therein.

9. The process as defined by claim 1, said butadiene concentration comprising at least 0.5% by weight of said medium of reaction.

10. The process as defined by claim 1, wherein the concentration of butadiene in said medium of reaction comprises no greater than about 50% by weight thereof.

11. The process as defined by claim 10, carried out discontinuously, and wherein the concentration of butadiene in said medium of reaction comprises no greater than about 30% by weight thereof.

12. The process as defined by claim 10, carried out continuously, and wherein the concentration of butadiene in said medium of reaction comprises no greater than about 10% by weight thereof.

13. The process as defined by claim 1, said medium of reaction comprising 3-pentenoic acid.

14. The process as defined by claim 1, carried out at a temperature ranging from 60° C. to 230° C.

15. The process as defined by claim 14, carried out at a temperature ranging from 90° C. to 200° C.

16. The process as defined by claim 1, said crotyl chloride being formed, in situ, from said butadiene or derivative thereof and hydrochloric acid.

17. The process as defined by claim 1, said palladium/crotyl pi-complex being formed, in situ, from said butadiene or derivative thereof and from a palladium salt which is soluble in said medium of reaction.

18. The process as defined by claim 1, wherein the concentration of water in said medium of reaction comprises no greater than about 8% by weight thereof.

19. The process as defined by claim 1, wherein the concentration of water in said medium of reaction comprises no greater than about 5% by weight thereof.

20. The process as defined by claim 1, wherein the overall Cl/Pd molar ratio in said medium of reaction is no greater than 100.

21. The process as defined by claim 20, wherein the overall Cl/Pd molar ratio in said medium of reaction is no greater than 20.

22. The process as defined by claim 1, for the preparation of 3-pentenoic acid.

* * * * *